US006738659B2

(12) United States Patent
Hsu (10) Patent No.: US 6,738,659 B2
(45) Date of Patent: May 18, 2004

(54) OPTICAL IMAGING USING THE TEMPORAL DIRECT REFLECTIVE SIGNAL FROM A MINIMIZED PULSE WIDTH LASER

(76) Inventor: Pei-feng Hsu, 736 Huntington St., Palm Bay, FL (US) 32907

( * ) Notice: Subject to any disclaimer, the term of this patent is extended or adjusted under 35 U.S.C. 154(b) by 465 days.

(21) Appl. No.: 09/941,516

(22) Filed: Aug. 28, 2001

(65) Prior Publication Data

US 2002/0065469 A1 May 30, 2002

Related U.S. Application Data (60) Provisional application No. 60/229,632, filed on Aug. 31, 2000.

(51) Int. Cl.[7] .................................................. A61B 6/00
(52) U.S. Cl. ....................... 600/478; 600/407; 600/476; 600/473
(58) Field of Search ................. 600/478, 407, 600/476, 473, 477, 475; 607/89, 72; 606/2, 15, 16

(56) References Cited

U.S. PATENT DOCUMENTS

| 5,921,926 | A | * | 7/1999 | Rolland et al. ............. 600/407 |
|---|---|---|---|---|
| 6,141,577 | A | * | 10/2000 | Rolland et al. ............. 600/407 |
| 6,370,422 | B1 | * | 4/2002 | Richards-ortum et al. ................. 600/478 |
| 6,381,490 | B1 | * | 4/2002 | Ostrovsky .................... 600/478 |
| 6,564,087 | B1 | * | 5/2003 | Pitris et al. .................. 600/478 |
| 6,564,089 | B2 | * | 5/2003 | Izatt et al. ................... 600/478 |
| 6,615,072 | B1 | * | 9/2003 | Izatt et al. ................... 600/478 |
| 6,654,630 | B2 | * | 11/2003 | Zuluaga et al. ............. 600/476 |

* cited by examiner

Primary Examiner—Henry Bennett
Assistant Examiner—Fadi H. Dahbour
(74) Attorney, Agent, or Firm—Joel I. Rosenblatt (57) ABSTRACT

A laser is used to radiate a non-homogeneous body comprising two or more materials, with varying scattering characteristics with reference to the radiation. The ballistic or snake radiation is detected as reflected radiation form incident points in the radiation light path and use to construct data indicative of one or more features of the body such as the interface between two of the varying characteristic materials which are in the radiation light path.

30 Claims, 4 Drawing Sheets

OPTICAL IMAGING USING THE TEMPORAL DIRECT REFLECTIVE SIGNAL FROM A MINIMIZED PULSE WIDTH LASER

CROSS REFERENCE TO RELATED APPLICATIONS

This application is related to Provisional Patent Application No. 60/229,632 filed on Aug. 31, 2000, for Optical Imaging Using The Temporal Direct Reflectance Signal From the Short Pulse Laser, Inventor Pei-feng Hsu, and claims as a filing date, the filing date the Provisional Patent Application of Aug. 31, 2000, from which this application is converted.

STATEMENT REGARDING FEDERALLY SPONSORED RESEARCH OR DEVELOPMENT

None

FIELD OF THE INVENTION

This invention is in the field of non-intrusively analyzing variations or changes in the different scattering mediums within a non-homogeneous body, by the use of collimated light pulse with a pre-determined pulse duration to illuminate the mediums and by detection of the varying scattering effects on the light produced by the variations in the mediums scattering characteristics.

BACKGROUND OF THE INVENTION

There exist many systems using collimated light from a laser source to illuminate a subject and then by analyzing the light as affected by subject, to determine one or several properties or characteristics of the subject. For example, as shown in U.S. Pat. No. 5,995,866, a short pulse of laser radiation is directed at a subject, which may be tissues, liquids, gases, or solid particles in a suspension, and light reflected or scattered from the subject is scanned by an electro-optical imaging means to generate image signals. Light from the subject causing variable fluorescence or spectral radiation, is detected as varying signals which are processed to detect cancerous cells, to quantize the cells as to number, shape or distribution, and to the stage of development.

U.S. Pat. No. 6,205,353 uses a group of sources of light at different wavelengths and detectors to generate a plurality of time resolved intensity data of back-scattered light from a highly scattered turbid medium and a reconstruction algorithm to reconstruct an image of the medium.

U.S. Pat. No. 5,949,077 shows how cancerous tissue within healthy tissue may be illuminated with collimated light from a laser source so the portion of the light transmitted though the cancerous tissue is captured as a shadow due to the varying absorption and scattering properties of the cancerous tissue relative to the healthy tissue. In the disclosed system, a light wavelength is chosen so an image is formed from the luminescent light from the subject and the light scattered by the scattering medium.

U.S. Pat. No. 5,813,988 uses a laser light source to illuminate a highly scattering turbid medium with a pulse of light. Light from the medium is received by a plurality of intersecting source/detecting sets in combination with time resolving equipment to produce a number of time-resolved intensity curves for the diffusive component of the light emerging from the medium over a relatively long period of time. Each of curves is processed according to an inverse reconstruction algorithm to form an image of the subject.

U.S. Pat. No. 5,140,463 discloses a system for improving the signal to noise ratio of an image signal produced by directing collimated light to an image hidden within a highly scattering semi opaque disordered medium by using space gated imaging or time gated imaging.

U.S. Pat. No. 5,799,656 produces an image of a subject located in or behind a turbid media, such as for example, in the cancer screening of breasts. It utilizes a special property of calcification in breast tissues that are suggestive of cancers and which can be discovered using optical imaging, with time and space gating of the light emerging from the illuminated medium.

U.S. Pat. No. 5,735,276 is similar to U.S. Pat. No. 5,995,866 in its use of collimated light and computer analysis of reflected and fluorescent light from the illuminated subject.

In addition to the patented systems described above, other methods and systems have attempted to use light in different diagnostic methodologies because of its low cost and its non-intrusive and non-ionizing radiation effects. While short pulse lasers were used, the focus of these systems was on analysis of the effect of the subject or probed material on the long term or diffusive component of emerging light or steady state light transmitted through the illuminated material or on the effect of the subject or probed material on the light altered by the transmittance characteristics of the subject material. A disadvantage of these systems is the derived transmittance signal lacks a direct precise correlation between the property of the light illuminating the subject scattering and absorbing medium, for example a tumor, with different transmittance characteristics relative to its surrounding normal tissue, and the different effects or the varying effects on the radiated light produced by the related varying characteristics of the tumor and normal tissue, requiring a complex inverse analysis algorithm to reconstruct the Image.

In the case of scattered or reflected light, relative to the incident light, the temporal profile of the different reflectance signals produced by the different effects of materials with varying scattering characteristics such as a tumor inclusion, and the surrounding medium such as normal tissue, on the light radiation, can be correlated with the spatial distribution of the inclusion. However, there is no capability for processing the reflected signal received from scattering mediums and comprised substantially of the ballistic light photons, traversing the shortest path and carrying the most information, about the scattering mediums, for example a tumor within healthy tissue, with the varying reflectance characteristics of the mediums.

While short pulse width lasers have been used in an attempt to detect enclosed or materials surrounded by partially opaque or turbid mediums, such as a tumor within healthy tissue, the short pulse width laser has not been used in a way that optimizes the recovery of information from the directly reflected signal and provides a detectable signal capable of producing more accurate and precise information at small material sizes, such as the initial growth stages of a cancerous tumor in healthy tissue.

SUMMARY OF THE INVENTION

This invention overcomes the disadvantages of prior art systems that use radiation, such as collimated light from a laser to illuminate a non-homogeneous body, comprising materials with varying light reflectance or transmission or scattering, characteristics, relative to each of the other materials, for producing data indicative of the size, location or image, of the materials enclosed or hidden by the scattering turbid medium of another of the non-homogeneous body's materials. This invention overcomes the prior art systems' disadvantages by illuminating the materials with a radiation pulse having a temporal pulse width minimized, relative to a combined factor $t_p^*$ related to the materials absorption coefficient and speed of propagation for the radiation.

Accordingly, it is an object of this invention, to detect the presence of at least one subject material or subject body or probed body located within or hidden or enclosed by another enclosing material or hiding material, and where the materials are of varying or different light scattering or reflective characteristics so the variations produced by the varying scattering mediums of the respective materials on the radiation, may be detected, analyzed or processed to produce at least one indicator comprising data or displays of the location or size or image, or other measurable indicia of the materials.

It is another object of this invention, to increase the accuracy and precision of the of the reflected signals in detecting an enclosed subject material, enclosed or hidden from the source of radiation, by an enclosing material or layer of material, between the subject material and the source of radiation, by selecting a temporal pulse width $t_p$ so the combined factor, $t_p^*$ as described below, of the light pulse width $t_p$, the extinction coefficient κ for the materials comprised by the materials in a non-homogeneous body, and the propagation speed c of the radiated light through the materials, is selected to minimize combined factor $t_p^*$ or to a value no larger than about 1.

It is another object of this invention to employ a data acquisition system to receive and process perspective related reflected radiation from a non-homogeneous body and the materials within, to construct a two or three dimensional image of a material in the path of the radiation, hidden or separated from the radiation directly on the non-homogeneous body by another of the non-homogeneous body's materials.

The inventive principles as disclosed herein is of a system and method for producing human readable information in data, for example in a visual display or in any other forms of perceptible data, relative to a non-homogeneous body comprising at least a first material enclosing or hiding a second material enclosed or hidden by the first material as for example an inclusion in a scattering turbid medium such as tissue material, where the materials are of different or varying reflectance or scattering characteristics.

By non-homogeneous body is meant a body comprising respective materials of different or varying radiation scattering characteristics. By enclosed material or hidden material or body, is means a material or body or inclusion enclosed by another material, comprised by the non-homogeneous body, enclosing or hiding the enclosed or hidden from the path of radiation and so the path of radiation is through the enclosed material or hiding material to the enclosed material or hidden material, and the path of the directly reflected radiation is from a respective incident point in the non-homogeneous material. By varying materials is meant materials having relative variations between the scattering characteristics of the radiated materials in the radiation path, for example as explained in *Advances in Optical Imaging of Biomedical Media*, by R. R. Alfano, S. G. Demos and S. K. Gayen, published in *Annals New York Acad. Sci.*, 1997, Vol. 820(2), pp. 248–270, incorporated in, and made a part of, this application.

As explained in *Advances in Optical Imaging of Biomedical Media*, an ultra short radiation pulse, may be used to illuminate a non-homogeneous body, and an image may be constructed substantially from the reflected ballistic or coherently scattered photons reflected from the varying or different scattering mediums within the body and which traverse the shortest path, carrying significant information about the materials in the radiation path.

In accordance with the description of a preferred embodiment and the principles of the disclosed invention, as describe herein, by temporal pulse width, is meant a pulse width $t_p$ measured in time relative to a combined factor $t_p^*$, as explained below and selected to minimize the value of $t_p^*$ or to limit $t_p^*$ to a value no greater than about 1. By combined factor $t_p^*$ is meant the factor $t_p^*$=κc $t_p$ where $t_p$ represents the pulse width, and c represents the speed of propagation of the radiation through the non-homogeneous body's materials and κ represents the extinction coefficient of the materials, which is related to the materials' absorption coefficient a and scattering coefficient σ, by the relationship κ=a+σ. According to the inventive principles, the pulse width $t_p$, is selected so the combined factor $t_p^*$ is minimized with respect to the materials extinction coefficientκ and speed of propagation, c or selected so the combined factor $t_p^*$ is no greater than about 1.

As shown in a preferred embodiment, $t_p^*$ is minimized or limited to a value no greater than about 1, to produce one or more indicators of selected indicia or properties of a non-homogeneous body, by detecting the directly reflected radiation from the respective incident points, as explained below, for example on the interface between an enclosing or hiding material and an enclosed material, such as an inclusion, with different or varying scattering characteristics, relative to each other, as explained herein, and which serves to prevent masking of the material by multiple scattering of photons reflected from the materials and to reveal with precision the details of a subject body within the enclosing material.

As would be apparent to those skilled in the art, the varying materials may not be fully enclosed or enclosing but arranged in layers so the material of interest such as an inclusion, is separated from the source of radiation by another of materials. By interface is meant the boundary between materials with varying scattering characteristics which produces variations in the reflected light, from the incident points on the radiation path. By incident points is meant the respective points in the non-homogeneous body along the radiation path from which the radiation is reflected directly back, for example through an enclosing material through an interface to an enclosing material, through enclosing material to the enclosing material on the other side or back side of the enclosed material and which respectively reflect the radiation, according to the respective scattering characteristics of the respective enclosing and enclosed materials.

By indicator is meant one or more indications of any measurable indicia for the material or materials of the non-homogeneous body derived in any way from perceptible data detected and acquired responsive to the reflected light from the incident points, from any system or method now or hereafter in existence.

According to the disclose inventive principles, what is shown is a system and method for optical imaging which uses a source of radiation to radiate a non-homogeneous body, comprising a plurality of materials with varying scattering mediums, where the laser temporal pulse width $t_p$ is selected so the combined factor $t_p^*$=κc $t_p$, is a minimum value or to a value no greater than about 1, where κ represents said extinction coefficient of said scattering mediums, and c represents the propagation speed of light radiation through the scattering mediums, and where a data detector receives the radiation reflected by respective incident points located in said radiation path, producing an indicator for at least one of the materials in the radiation path.

The radiated energy in the form of photons traveling in waves, enter the non-homogeneous body and are scattered by the varying materials, as explained above, within the non-homogeneous body and as would be know to those skilled in the art, and as explained with reference to *Advances in Optical Imaging of Biomedical Media* by Alfano et al., incorporated herein. Where an enclosing or hiding material has a different or varying scattering coefficient, σ, the reflected or scattered light varies in accordance with the variation in the materials scattering coefficients $\sigma_1$ and $\sigma_2$, respectively. At the interface, for example, between the varying materials, where there is a change in the respective material's scattering coefficients, $\sigma_1$ and $\sigma_2$, the characteristics of the reflected light will change responsive to the relative changes in the scattering coefficients, $\sigma_1$ and $\sigma_2$, accordingly. When the reflected radiation is time resolved relative to the distance traveled of the radiation in the radiation path, the location of the interface between the first and second varying may be detected, as a change in the reflected radiation. As shown for a preferred embodiment the scattering coefficient $\sigma_1$ for the enclosing material comprised by the non-homogeneous body, is less than the scattering coefficient $\sigma_2$ for the enclosed or hidden material comprised by the non-homogeneous body.

By detecting and resolving the reflected radiation with respect to time, the changes in the reflected radiation produced by incident points at the interface for example, or at any other location in the non-homogeneous body, may be analyzed to produce an indicator of the size, location or image of the interface or other materials or locations of interest in the non-homogeneous body.

As would be apparent to those skilled in the art, the disclosed invention is not limited but may be applied to the imaging of any non-homogeneous body comprising materials with relative varying scattering characteristics and may be used with detector or data acquisition systems now or hereafter in existence which would be capable of detecting the reflected light and producing perceptible data for an indicator of the size, location or image or other indicia of at least one of the materials.

These and other objects and advantages of the disclosed invention shown in a preferred embodiment according to the inventive principles, will become apparent to those skilled in the art upon reading the following Description of the Preferred Embodiment.

DETAILED DESCRIPTION OF THE INVENTION

The inventive principles are shown with reference to disclosed invention as shown in a preferred embodiment.

Figure 1:
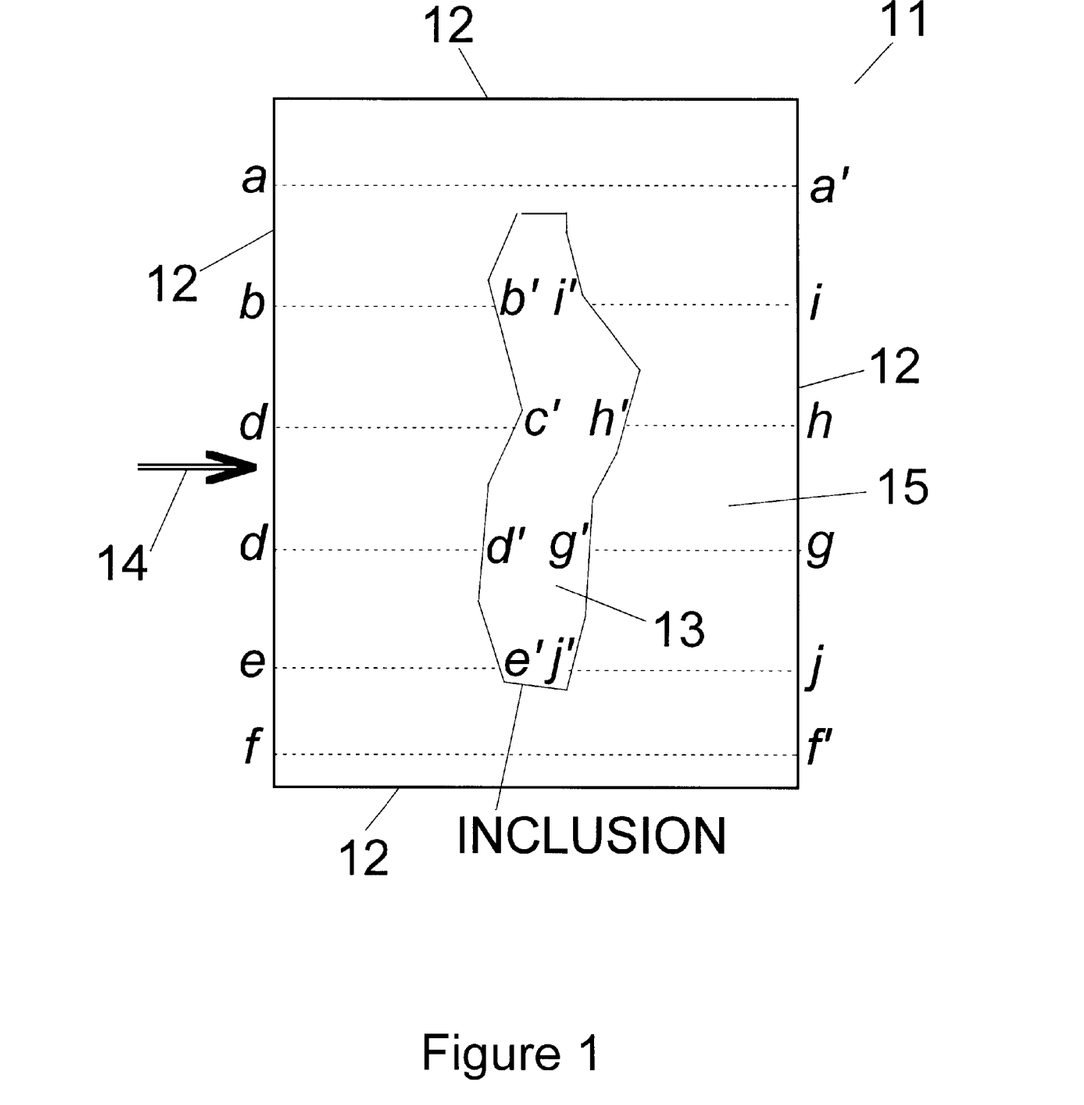
FIG. 1 shows a non-homogeneous body comprising an enclosing material and within the enclosing material an enclosed subject body, the materials having varying or different reflectance or scattering characteristics, relative to each other and with examples for the incident points of radiation on the homogeneous body, the enclosing body and the subject body shown as an inclusion.

The object of this disclosed invention is to locate and display all of the relevant data such a location, size, or image, or other indicia, of materials having varying scattering characteristics, for example an inclusion, as shown in FIG. 1, of a subject enclosed material or body 13 enclosed in enclosing material 15 within a non-homogeneous material or body 11. As would be apparent to those skilled in the art, the boundary 12 of the enclosing material 15 within the non-homogeneous body 11 are as defined by the continuous line from points a to f and from f' to a' and from a' to a, while the inclusion 13 shown as the enclosed material within the non-homogeneous body 11 is defined by the continuous line from points b' to e', from j' to i', for the example shown. In the example used in the description of the inventive principles according to a preferred embodiment, each of the points are examples of incident points of radiation on the respective materials and responsive to the radiation, each of the incident points are scattering points reflecting light back to the source of radiation. As would be apparent to those skilled in the art, the incident points are used by way of example, it being understood that a scattering medium in the path of radiation will produce scattering of the incident radiation at any point within the radiation path and each respective point in the medium will be an incident point, according to the disclosed principles.

In the example shown, the direction of incident radiation is as shown by arrow 14, and the radiation incident points are shown as a–f, f–f'. f–a' and a'–a, for the medium shown by the enclosing material 15 and b'–e', e' to j', j'–l' and l'–a', for the medium shown by the inclusion or enclosed material 13. Those skilled in the art will recognize the incident points may be any location in the radiated which scatters the incident radiation, as explained above and the number of incident points may expanded to increase the resolution of the resultant data detected from the reflected light or may be rotated or translated relative to the source of radiation for expanding the incident points of radiation, as shown and described with reference to FIG. 2, for producing multidimensional images of the body.

Figure 2:
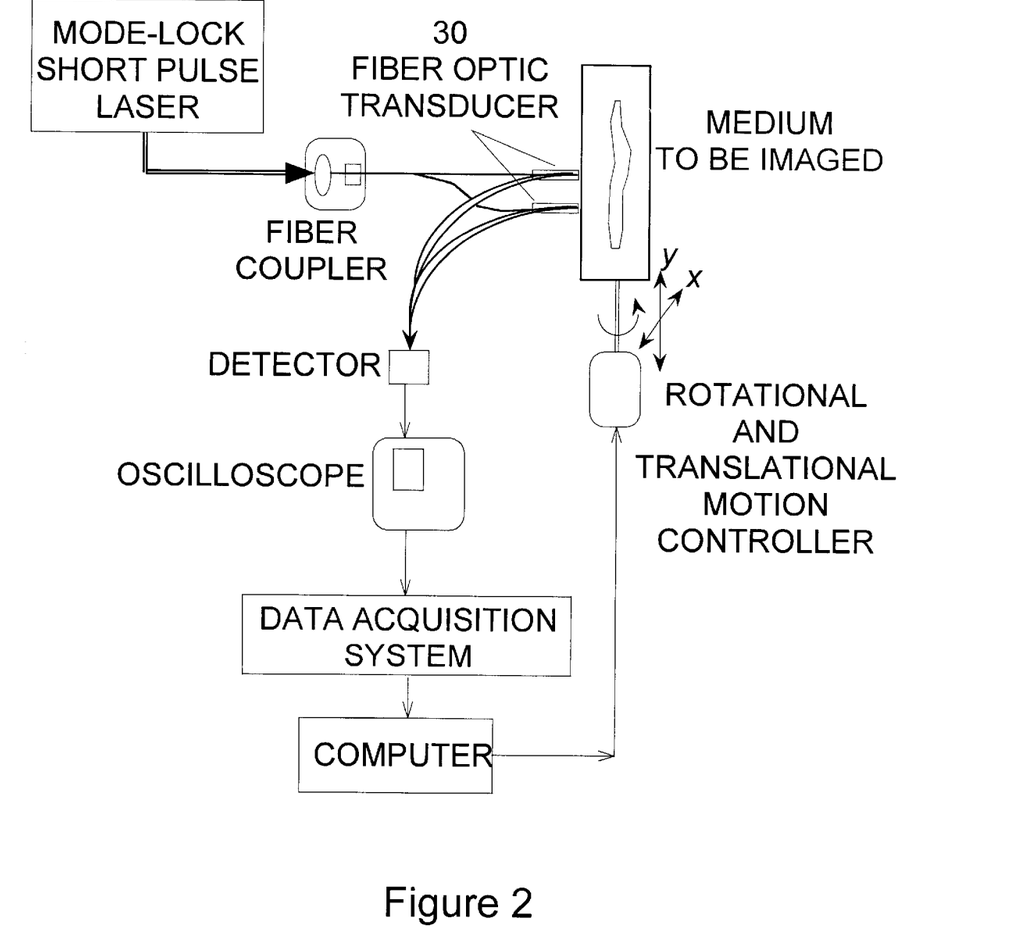
FIG. 2 shows a Detector and Data Acquisition System for radiating the non-homogeneous body shown in FIG. 1 with a light radiation from a short pulse width laser and over a plurality of points and perspectives, by translating or rotating the body relative to the light radiation and for directly receiving and detecting the scattered reflected light from the non-homogeneous body and analyzing it to display in an indicator, perceptible data showing the inclusion or enclosed subject body.

As would be apparent to those skilled in the art, the incident points would include all of the points in the scattering material in the path of the radiation and responsive to that received radiation, capable of scattering the radiation and reflecting radiation to the detector in the Detector and Data Acquisition System shown in FIG. 2.

While the non-homogeneous body 11 and the enclosing material 15 and enclosed inclusion 13, may be any materials capable of receiving and reflecting the incident radiation, in connection with the description of a preferred embodiment, as an example, a tumor is used for the material shown as an inclusion and as the enclosed material 13, enclosed within the medium shown by enclosing material 15, comprised by the non-homogeneous body 11.

FIG. 2 shows a Data Detector and Acquisition System according to the example shown in a disclosed preferred embodiment, for radiating the non-homogeneous body 11 with radiation from a laser for example and for receiving the directly reflected radiation scattered by the incident points in the path of the radiation. For the purpose of explanation, the enclosed material 13 may be described as the subject material, as well as the inclusion or enclosed material 13. In operation of the inventive principles, the radiation is directed at defined incident points shown by way of example, the incident points in FIG. 1 and which may be expanded as shown in FIG. 2 by a rotational and translation motion controller, for providing sufficient reflected light signals in relation to the surface area of the inclusion 13 to accumulate sufficient data to display and define the inclusion 13 in a two or three dimensional structure.

As shown in FIG. 2, the Data Detection and Acquisition System my use a single optical fiber transducer 30, as described with reference to FIGS. 3 and 3a, or a plurality of these transducers 30, operated by the Detection and Acquisition System as explained herein. For the purposes of explanation, two transducers 30 are shown. However, according to the inventive principles disclosed for a preferred embodiment, one or more transducers 30 may be used as explained herein. When operating a plurality of transducers, the radiation from each transducer is directed in a separate respective path to a respective location on the non-homogeneous body, for example, the body 11 shown in FIG. 1, and the Data Acquisition System Computer then is programmed to correlate the position of each of the radiation paths on the non-homogeneous body with the respective reflected radiation to produce data indicative of the reflected radiation and optical distance, as explained below, for respective incident points in the radiation paths, as explained below, to construct a one or two or three dimensional image for the non-homogeneous body, for example, the image of an interface between an enclosed material in the non-homogeneous body and the enclosing material in the non-homogeneous body, enclosing the enclosed material, as would be known to those skilled in the art.

Figure 3:
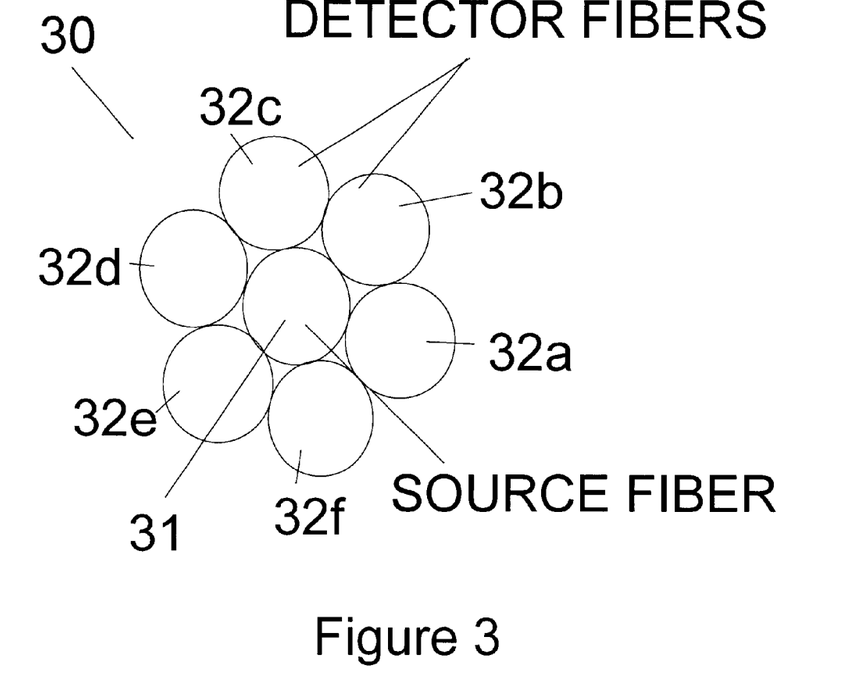
FIG. 3 shows the fiber optic transducer for transmitting light radiation to the non-homogeneous body and to its enclosing material and the enclosed subject material shown as an inclusion and for directly receiving the back-scattered or reflectance light, from the materials within the non-homogeneous body.
Figure 3A:
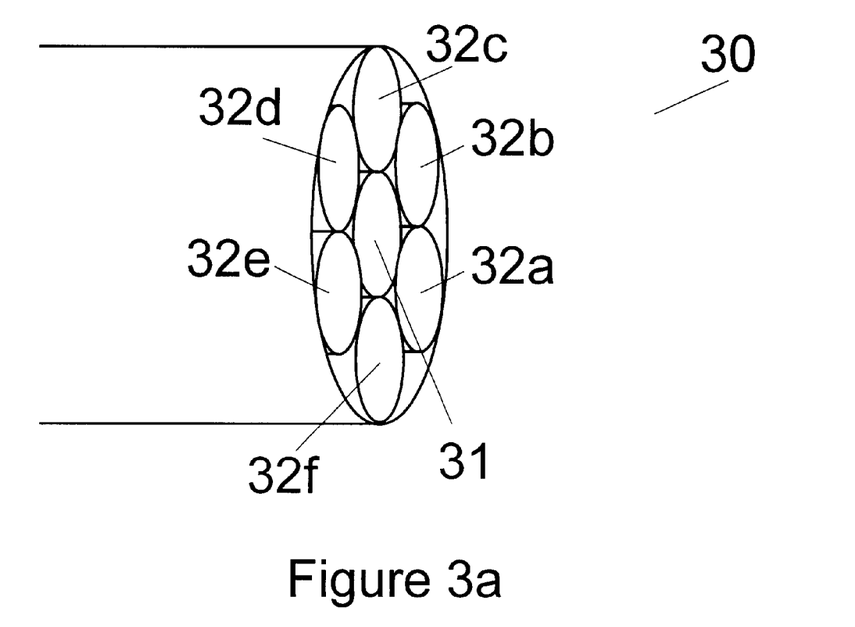
FIG. 3a shows in a perspective view, the face of the fiber optic transducer shown in FIG. 3.

In order to be able to receive the reflected signals directly reflected from the enclosing material 15 and subject material shown as inclusion 13 an optical transducer as shown in FIG. 2, in shown in greater detail in FIG. 3. The fiber optic bundle or transducer 30 shown in FIGS. 2 and 3, for transmitting the short width laser light pulse and for receiving the responsive reflected radiation from the non-homogeneous body 11, is shown in schematic form in FIG. 3. The end of the fiber bundle is shown with the face of each fiber from which the source light is radiated or the reflected light is received, is shown as lying in the plane of the page. As shown, a center fiber, 31 is used as the source of light radiation and surrounding fibers 32a to 32f are used to collect the reflectance light signal for analysis by the Detector and Data Acquisition System, shown in FIG. 2. The light processed by the Detector can be directly received by the Detection fibers in an angular range from the 0 degree axis perpendicular to the face of the fiber optics shown in FIG. 3, to an angle with reference to the 0 degree axis at which a light reflectance signal can be detected and analyzed to provide an indicator as described below of perceptible data indicative of the inclusion or enclosed body size, mage or location within the non-homogeneous body 11. Any system now existing or which may exist in the future for detecting and processing the reflectance signal within that angular range may be used. For increasing the efficiency of the inventive process, one or a plurality of optical bundles or transducers 30 as shown in FIG. 3 and as shown as used in FIG. 2, can be used for producing the indicator or indicators of the radiated materials, without departing from the disclosed inventive principles.

As shown, a bundle of optical transducer 30 contains a source fiber 31 surrounded by detection fibers 32a to 32f. As would be apparent to one skilled in the art, the arrangement of the fibers may be varied without departing from the principles of the disclosed invention, provided the transducer is capable or receiving the directly reflected light signals from each of the incident points, shown by way of example in FIG. 1. By directly receiving as describe above is meant receiving the reflected or scattered light from the body 11, in range from 0 degrees referenced to the longitudinal axis of the detection fibers 32a to 32f, at the face of the fibers, as shown in FIG. 3 to be in the plane of the paper, to the widest angle at which reflected or scattered light is capable of being detected by a data detection and acquisition system in existence now or hereafter, to produce as perceptible data an indicator, indicative of the size, location and image or other indicia, of the inclusion or the interface between the enclosing material 15 and the subject enclosed inclusion 13. As would be apparent to those skilled in the art, with the arrangement shown for a preferred embodiment in FIG. 3, the detection fibers 32a to 32f are arranged about the 0 degree axis of the radiated light from the source fiber 31 and the scattered light reflected from the scattering medium in the non-homogeneous body 11 would be reflected at an angle offset from the respective detection fiber's 0 degree axis.

Figure 4:
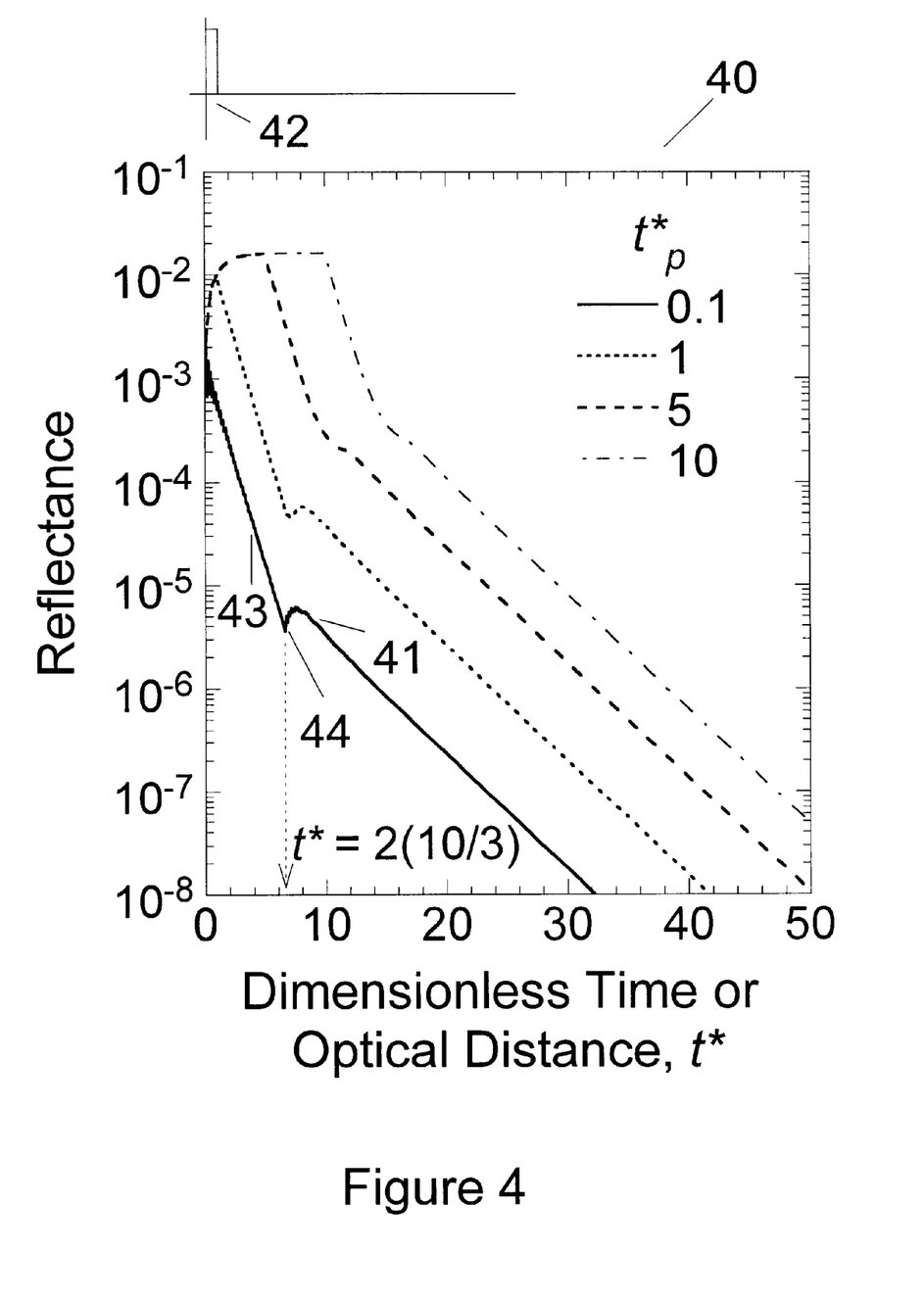
FIG. 4 shows the temporal responses of radiation reflected or back-scattered from the non-homogeneous body shown in FIG. 1, showing the relative strength of the direct reflected radiation, on a logarithm base 10 scale, from the enclosing material and with the enclosed material having enclosed therein an enclosed material shown as an inclusion in FIG. 1, normalized for different values of the combined factors $t_p^*$, for the respective selected pulse width $t_p$, and shown with the optical distance t* reference a pulse of radiation.

The particular equipment which may be used in the system shown in FIG. 2, according to the disclosed inventive principles, would be well known to those skilled in the art and for that reason are disclosed in detail. As would be known to those skilled in the art, a short pulse width laser may be used as a source of radiation. The reflected radiation detector may be a streak camera as manufactured by Hamamatsu Photonics, K.K. Systems Division, Japan, as would be known by those skilled in the art, and used in connection with a suitably programmed general purpose computer to process the signals produced responsively to produce as perceptible data, an indicator, for example as shown in FIG. 4, of the interface between the inclusion 13 and the enclosing material 15.

The disclosed principles of the invention, are explained with reference to the preceding description and to the disclosure entitled *An Integral Formulation of Transient Radiative Transfer* by Z.-M. Tan and P.-f. Hsu, published in American Society of Mechanical Engineers *J. Heat Transfer*, June 2001, Vol. 123, pp. 466 to 475 and incorporated by reference as a part of this application as if repeated in its entirety, herein. As shown, therein.

The equation for transient radiative transfer of the intensity/in direction ŝ, position z, and time t is given by (*Thermal Radiation Heat Transfer* by Siegel and Howell (1992), Hemisphere Publishing, Washington D.C.)

$$\frac{dI(z, \hat{s}, t)}{ds} = \frac{DI(z, \hat{s}, t)}{cDt} \tag{1a}$$
$$= -\kappa I(z, \hat{s}, t) + aI_b(z, t) +$$
$$\frac{\sigma}{4\pi} \int_{\Omega'=4\pi} I(z, \hat{s}', t)\Phi(\hat{s}', \hat{s})d\Omega'$$

or $$\frac{\partial I(s, \hat{s}, t)}{c\partial t} + \frac{\partial I(s, \hat{s}, t)}{\partial s} = -\kappa I(z, \hat{s}, t) + aI_b(z, t) + \tag{1b}$$
$$\frac{\sigma}{4\pi} \int_{\Omega'=4\pi} I(z, \hat{s}', t)\Phi(\hat{s}', \hat{s})d\Omega'$$

where the D symbol represents the substantial derivative. $I_b$ is the blackbody intensity, a the absorption coefficient, $\sigma$ the scattering coefficient, $\kappa$ the extinction coefficient ($\kappa=a+\sigma$), $\Phi$ the scattering phase function, and $\Omega$ the solid angle. c is the light speed in the medium. Equation (1a) is the Lagrangian viewpoint and Eq. (1b) the Eulerian. Except for simple geometry and boundary condition, analytical solution of Eq.

(1) is impossible. Many optical imaging researches have so far relied on approximate methods to solve Eq. (1). For example, the diffusion approximation is widely used to find the temporal radiative signals emerging from the pulse-laser irradiated medium. However, large discrepancy with the experiment results and other solution methods was found in the signals near the initial transients, which offer the most information regarding the medium's composition. The initial transient signals contain mostly the coherent part of the incident laser, i.e., the ballistic and snake photons (*Advanced in Optical Imaging of Biomedical Media* by Alfano, et al. (1997), *Anna. NY Acad. Sci.*, 820(3): 248–270). The diffusion approximation fails to predict the initial transient results. There are several other approximate analytical solutions that have been applied to solve the light pulse propagation within the scattering medium but all with limited success.

An exact, analytical solution using integral equation formulation of Eq. (1a) is described herein. The substantial derivative on the left-hand side of Eq. (1a) allows the expression of, in the Eulerian variable, a time derivative as one follows a specific photon. It is found that the Lagrangian viewpoint can simplify the analysis of the time-of-flight of a photon and allows for the deduction of the analytical form of the solutions. Since in the Lagrangian viewpoint the observer is moving with the wave, the dependence upon s and t could not be separated from each other. The dependence is evident from the relationship of dt=ds/c. Therefore, only one independent variable (either t or s) is needed in the Lagrangian analysis. When a radiation beam travels through a participating medium, it is attenuated by absorption and by out-scattering and at the same time gains energy by in-scattering from other directions into the direction of travel. The photon transport process is described by Eq. (1). Once the distance ds through which the radiation travels along a certain path is given, the relative location s+ds and the time interval dt=ds/c (hence the instant t'=t+ds/c) can be determined definitely.

To begin with, the physical case under consideration is one-dimensional slab of an absorbing, non-emitting, and scattering medium. In the derivation below, the radiative properties are nonhomogeneous, i.e., function of position z. The same development has been extended to the multi-dimensional geometry (*Transient Radiative Transfer in a Three-Dimensional Participating Medium*, by Z.-M. Tan, and P.-f. Hsu in the Proceedings of the Third International Symposium Radiative Transfer, Antalya, Turkey, June 2001), incorporated by reference herein. The slab thickness is $z_o$ in the z direction. The transient radiative transfer equation can be written as (using the Lagrangian viewpoint of Eq. (1a))

$$\frac{dI(z,\hat{s},t)}{ds} = -\kappa(z)I(z,\hat{s},t) + \frac{\sigma(z)}{4\pi}\int_{\Omega=4\pi} I(z,\hat{s}',t)\Phi(\hat{s}',\hat{s})d\Omega \tag{2}$$

For isotropic scattering, $\Phi(\hat{s}',\hat{s})=1$. This leads to $$\frac{dI(z,\hat{s},t)}{ds} = -\kappa(z)I(z,\hat{s},t) + \frac{\sigma(z)}{4\pi}G(z,t) \tag{3}$$

where G(z,t) is the incident radiation (or integrated intensity) defined as $$G(z,t) = \int_{4\pi} I(z,\hat{s}',t)d\Omega \tag{4}$$

Integrating Eq. (3) on both sides, one obtains $$I(z,\hat{s},t) = I(0,\hat{s},t-s/c)e^{-\kappa s} + \tag{5}$$

$$e^{-\kappa s}\int_{s'=0}^{s'=s}\frac{\sigma(z')}{4\pi}G(z',t')e^{\kappa s'}ds'$$

In order to carry out the integration on the right side of Eq. (5), the dummy variables z' and t' of G function should be expressed in terms of the path length variable s'. The details are given in the afro-mentioned articles by Tan and Hsu. With the new relations for z' and t', Eq. (5) becomes:

$$I(z,\hat{s},t) = I(0,\hat{s},t-s/c)e^{-\kappa s} + \tag{6}$$

$$\frac{1}{4\pi}\int_0^s \sigma(z')G(z-(s-s')\cos(\hat{s},\hat{k}),t-$$

$$(s-s')/c)e^{-\kappa(s-s')}ds'$$

Physically, the first term on the right-hand side of Eq. (6) is the contribution to the local intensity by the intensity entering the medium from the boundary at s'=0, which decays exponentially due to extinction over the optical distance κs (FIG. 1). Since it takes the photon an amount of time s/c to travel from the boundary (at s'=0) to the point under consideration (at s'=s), the boundary contribution can only come from the radiation entering the medium at an earlier instant of t'=t−s/c. The integrand of the second term, σG(z',t')ds'/4π, is the contribution from the local scattering at s', attenuated exponentially by extinction over the distance between the scattering point and the point under consideration, s−s'. Since the time interval between these two points is Δt=(s−s')/c, only the photons at and after the instant of t'=t−(s−s')/c and in the position z'≧z−(s−s')cos(ŝ,k̂) contribute to the radiative intensity at the location z and the instant t, I(z,ŝ,t). The integral sums all of the contributions over the entire scattering path from s'=0 to s'=s. Equation (6) shows that the intensity in a certain direction depends on the time history along the path in that direction. Furthermore, I(z,ŝ,t) depends on the radiation emitted from the boundary at an earlier instant t−s/c in the same direction and the entire time history of incident radiation along the path of travel, rather than the intensities at the same instant t. Thus, transient radiative transfer presents a strong time dependence, which in turn implies a path length dependence. It should be noted that after appropriate transformation and differentiation, Eq. (6) can be reduced to Eq. (1b).

Integrating Eq. (6) over all 4π solid angle gives $$G(z,t) = \int_{4\pi} I(0,\hat{s},t-s/c)e^{-\kappa s}d\Omega + \tag{7}$$

$$\frac{1}{4\pi}\int_{4\pi}\left[\int_0^s \sigma(z')G(z-(s-s')\cos(\hat{s},\hat{k}),t-(s-s')/c)e^{-\kappa(s-s')}ds'\right]d\Omega$$

-continued $$= \iint_{A(t)} \frac{I(0, \hat{s}, t - s/c)e^{-\kappa s}}{s^2} \cos(\hat{n}, \hat{s}) dA +$$

$$\frac{1}{4\pi} \iiint_{V(t)} \frac{\sigma(z')G(z - (s-s')\cos(\hat{s}, \hat{k}), t - (s-s')/c)e^{-\kappa(s-s')}}{(s-s')^2} dV$$

where $\hat{n}$ is the inward unit normal vector of the boundary surface. For higher order scattering phase function, similar integral formulation can be obtained (*Radiative Heat Transfer in Multidimensional Emitting, Absorbing, and Anisotropic Scattering Media— Mathematical Formulation and Numerical Method* by Z. Tan, ASME *J. Heat Transfer*, 1989, Vol. 111, pp. 141–146.).

The A(t) and V(t) specified in Eq. (7) need to be determined before solution of G function can be obtained. The determinations of A(t) and V(t) are given in the journal article by Tan and Hsu cited previously. With appropriate numerical quadratures, the G function is obtained exactly without any physical approximation to the transport equation. The only approximation involved will be due to the numerical integration, which can be easily minimized, and the details are discussed in the same article.

In the situation of the normally incident collimated laser pulse on one boundary and the other being cold and black or transparent, then $$I(0,\hat{s},t) = I_0[u(t) - u(t-t_p)]\hat{k}. \quad (8)$$

where u(t) is the unit step function, $t_p$ is the temporal pulse width and $\hat{k}$ is the unit vector into z-direction or the collimated laser incidence direction. In this case, Eq. (7) can be simplified as $$G(z, t) = I_0 u\left(t - \frac{z}{c}\right) e^{-\kappa z} + \quad (9)$$

$$\frac{1}{2} u\left(t - \frac{z}{c}\right) \int_{z'=0}^{z'_2} \int_{r=0}^{\sqrt{(ct-z)(ct+z-2z')}} \frac{\sigma(z')G(z', t'_2)e^{-\kappa\sqrt{(z-z')^2+r^2}}}{(z-z')^2 + r^2} r dr dz'$$

After solution of G function is obtained, then it can be substituted into Eq. (6) to obtain intensity at any position along any direction. FIG. 4 is the result of $l(z=0,-\hat{k},t)$ that provides the temporal reflectance signal. From this reflectance signal, once the appropriate pulse width of the pulse laser was determined, whether the medium contains inclusion or the location of the inclusion can be determined.

FIG. 4 shows the calculated reflectance signal normalized with respect to the magnitude of the incident laser pulse intensity. The figure demonstrates the effect of different incident pulse width on the temporal reflectance signal. Assume the optical fiber detector (FIG. 3) is placed at position b of FIG. 1. The distance bb' equals to l. The photons from the radiation source will move from b to b' and return back to b and will travel a total distance of 2l and take a total travel time of 2l/c. A convenient dimensionless quantity used frequently in radiation transport and optics is the optical distance, i.e., the product of extinction coefficient and a characteristic length. The characteristic length, in the case of FIG. 1, is the physical distance between any two points inside the medium. If the time (t) is normalized with respect to κ and c, then the resulting dimensionless quantity is equivalent to optical distance, i.e., $$t^* = \kappa c t \quad (10)$$

Therefore, if the travel time of b–b'–b is normalized in the same way, then $$t^* = \kappa c(2l/c) = 2/\kappa \quad (11)$$

From Eq. (11), it is evident that in FIG. 4 the horizontal axis not only represents the time, but also correlates to the l, which is the distance from the pulse laser incident boundary to the first interface between the inclusion and the surrounding medium.

The optical distance is defined as $\tau = \kappa L$, where L is the physical distance. In FIG. 1 the layered or slab medium has overall optical distance $\tau = 10$, in which the L equals to the distance of a–a'. The optical distance of b–b' is 10/3. As seen in FIG. 4, the display for a combined factor of $t_p^* = 0.1$ has a local minimum point occurs at $t^* = 20/3$, which is exactly twice the photon travel time from b to the first interface b' (bb'=10/3). Similar reflectance signal can also be observed in the display curve of $t_p^* = 1$. In fact, with smaller $t_p^*$, the effect is even more evident as long as the inclusion has larger scattering coefficient than the surrounding medium.

If the pulse is applied on the other boundary, for example the position i in FIG. 1, similar reflectance signal can reveal the second interface. Thus, the measurement of two direct reflectance temporal signals provides the location and extent of the inclusion along the line of sight. By scanning the medium over a plurality of locations, or using several fiber bundles strategically positioned around the medium, a complete image of the inclusion can be obtained. It should be pointed out that at large pulse widths, the local minimum of the temporal reflectance curve is masked by the multiple-scattered photons. It is therefore important to ensure the pulse's temporal width is short enough to reveal the spatial detail. $t_p^*$ can be also considered as the ratio of the length scale of the photon travel in the duration of pulse versus the mean free path of photon travel within the medium. As shown in the FIG. 4, to obtain the desirable signal the $t_p^*$ has to be equal or less than unity. The relation of $$t_p^* = \kappa c t_p < 1 \quad (12)$$

can be used to select an appropriate pulse width ($t_p$) given the medium extinction coefficient and the refractive index ($n = c_o/c$) at the probing wavelength.

In accordance with the principles of the disclosed invention, the reflected radiation from an incident point, produced by a short time width laser pulse selected so $t_p^*$ is minimized or in a range up to about 1, may be detected as an amplitude with respect to the optical distance of the incident point from the source of radiation. Where the respective incident point is on the interface between two materials such as 13 and 15 as described with reference to FIG. 1, a indicator 40 will appear in the amplitude with respect to the dimensionless time or optical distance of the interface from the source of radiation.

A single pulse of the radiation source may be used where the Data Detection and acquisition system is sensitive enough to produce a responsive amplitude plot of reflectance amplitude versus optical distance. Otherwise, the amplitude plot may be constructed from successive amplitude responses from respective single pulses of the radiation source.

As shown in FIG. 4, according to the principles of the invention as disclosed herein, an indicator produced from the detected data responsive to the reflectance radiation can produce the clearest and most perceptible data as shown by the data corresponding to the reflected radiation amplitude 40 where $t_p^* = \kappa c\, t_p$ is minimized, and can produce perceptible data 40 when or no more up to a value of $t_p^*$ of about 1. In operation of the invention, the data detection and acquisition system may be used with one or a plurality of radiation sources and associated detectors to produce a plurality of indicators for the enclosed material. A suitable general purpose computer programmed to sense the position of the radiation sources and associated detectors and to correlate the reflected radiation received with the respective incident point locations in the non-homogeneous body, as would be known to those skilled in the art would be used to operated the laser, detector and data acquisition system and the motion controller.

As show in FIG. 4, for a preferred embodiment, an indicator for an interface between two materials with different scattering characteristics may be any perceptible change in the reflected data responsive to a pulse of radiation shown by numeral 42, for example the dip 44, in the reflected radiation amplitude between the reflected amplitude for the enclosing material or hiding material, shown by numeral 43, and the enclosed material or hidden material, shown by numeral 41, is an indictor of of the interface between the enclosed and enclosing materials, with varying scattering characteristics. The display 40, represents the data produced by the data detector and acquisition system, as shown in FIG. 2, and as explained above, and as would be known to those skilled in the art.

The data shown displayed by FIG. 4, is in units of amplitude and in units of dimensionless time t*, or as explained herein, the optical distance. Accordingly, by dimensionless time is meant the normalized optical distance, explained herein.

While the inventive principles are described with reference to a minimum temporal pulse width for the source of radiation, the actual pulse width $t_p$ will depend on the minimum pulse width attainable by available pulsed radiation sources and the minimum energy requirements or sensitivity of available data detectors and processors to the reflected radiation, to produce perceptible data that, for example, is not masked by noise. A source of radiation which may be used in the practice of this invention is the TIGER Mode Locked Femtosecond Laser, produced by Time-Bandwidth Products, Zurich, Switzerland. As would be known to those skilled in the art, a fixed pulse width laser or a laser with a variable pulse width may be used to set the laser to the selected pulse width. In an example of the practice of the disclosed invention, according to the disclosed inventive principles, for detection of an inclusion within healthy human tissue such as breast tissue, the optical property data which may be used are as may be obtained from *Optical-Thermal Response of Laser-Irradiated Tissue*, ed. by A. J. Welch and M. J. C. Van Germert, 1995, Plenum Press, New York.

The average refractive index (n) of mammalian tissues is 1.41. The light propagation speed within the tissue is therefore, $$c = \frac{2.998 \cdot 10^{10} \text{ cm/s}}{1.41} = 2.126 \cdot 10^{10} \text{ cm/s} \quad (13)$$

At light pulse wavelength of 0.54 μm, the adipose breast tissue has scattering coefficient equal to 100 1/cm and absorption coefficient 2.3 1/cm. The extinction coefficient is 102.3 1/cm. For ductal carcinoma in breast, at the same wavelength the scattering coefficient is 190 1/cm and absorption coefficient is 3.1 1/cm. To determine an appropriate laser pulse width at this same wavelength, the pulse width can be determined from Eq. (12), i.e., $$t_p^* = \kappa c t_p < 1$$

or, $$t_p < 1/\kappa c = 1/(2.126 \cdot 10^{10} \text{ cm/s} \cdot 102.3 \text{ 1/cm}) = 460 \cdot 10^{-15} s = 460 \text{ fs} \quad (14)$$

Therefore, the appropriate laser pulse width for the example given, is below 460 femtosecond to detect the ductal carcinoma surrounded by adipose breast tissue.

As would be understood by those skilled in the art, the principles of the disclosed invention are not limited to the examples shown herein for a preferred embodiment but this invention may be practiced with any suitable equipment now or hereafter in existence.

What is claimed is:

1. A system for optical imaging using a pulse of radiation in a radiation path to an enclosed material within a non-homogeneous body and responsive to reflected radiation, producing an indicator for said enclosed material, comprising,
   a. means for producing one or more pulses of radiation, to radiate a plurality of materials with varying scattering mediums within a non-homogeneous body, in a radiation path, with at least one pulse of radiation of a temporal pulse width $t_p$;
   b. means for selecting said laser temporal pulse width $t_p$ in relation to a combined factor $t_p^* = \kappa \cdot c \cdot t_p$ for a minimum value for said combined factor $t_p^*$ or for a value of said combined factor $t_p^*$ no greater than about 1, where κ represents said extinction coefficient of said scattering mediums, and c represents the propagation speed of light radiation through said scattering mediums;
   c. means for receiving said reflected radiation from respective incident points located in said radiation path;
   d. means for producing an indicator for at least one material in said radiation path, responsive to said radiation reflected by said respective incident points.

2. The system of claim 1, wherein, said means for producing said indicator includes
   e. means for producing an indicator of the location of at least one of said respective incident points.

3. The system of claim 2, wherein said means for producing an indicator of the optical distance includes
   g. means for producing data indicative of the amplitude of said radiation reflected from said respective incident points and data indicative of the optical distance t* to said respective incident point, where the optical distance to said respective incident point is $t^* = \kappa \cdot c \cdot t$, and where l represents the distance of said radiation path to said respective incident point and where the effective time t of propagation for said respective incident point is $t = 2l/c$.

4. The system of claim 1, wherein said means for producing said indicator includes f. means for producing an indicator of the optical distance of said respective incident points.

5. The system of claim 1, wherein, h. said means for producing one or more pulses of radiation produces a single pulse of radiation; and i. said means for producing an indicator produces said indicator substantially in response to the ballistic scattered photons reflected from said respective incident points.

6. The system of claim 1, wherein, said means for producing an indicator comprises, j. means for producing an indicator indicative of the amplitude of said reflected radiation from said respective incident points and of the optical distance t* to said respective incident points.

7. The system of claim 1, wherein, k. said means for producing an indicator includes means for producing an indicator for an enclosed material in said path of radiation, enclosed by an enclosing material, in said path of radiation.

8. The system of claim 7, wherein, said means for producing an indicator includes detecting and data acquisition means for producing an indicator of the size, location or image of said enclosed material enclosed by said enclosing material.

9. The system of claim 8, wherein, said detecting and data acquisition means includes means for producing data displaying separate amplitudes for respective incident points in said radiation path and the corresponding optical distances t* of said respective incident points.

10. The system of claim 1, wherein, said means for producing an indicator, comprises, l. means for producing data of the reflected radiation amplitudes of the respective incident points correlated with the optical distance t* to the respective incident points;

m. means for displaying said indicator as a change in said data at an interface between an enclosed material enclosed by an enclosing material, of said plurality of materials.

11. The system of claim 10, wherein, said means for producing said indicator includes means for producing a single pulse of radiation, and said means for producing data includes means for receiving said reflected radiation substantially about the axis of said path of radiation.

12. The system of claim 1, wherein, n. said means for producing said radiation includes means for producing a single pulse of radiation; and o. said means for producing an indicator includes means for producing an indicator in response to said single pulse of radiation for at least one of said plurality of materials in said radiation path.

13. The system of claim 1, wherein, p. said means for producing radiation includes a plurality of means for producing radiation in a plurality of radiation paths and said means for receiving said reflected radiation includes a plurality of means for receiving reflected radiation from said plurality of radiation paths;

q. means for operating said plurality of means for producing radiation in a plurality or radiation paths and for operating said plurality of means for receiving reflected radiation from said plurality of radiation paths;

r. said means for producing an indicator includes means connected to said plurality of means for receiving reflected radiation from said plurality of radiation paths, and responsive to said reflected radiation, for producing said indicator from said reflected radiation from said plurality of radiation paths.

14. A method for optical imaging using a pulse of radiation in a radiation path to an enclosed material within a non-homogeneous body and responsive to reflected radiation, producing an indicator for said enclosed material, comprising, a. producing one or more pulses of radiation, to radiate a plurality of materials with varying scattering mediums within a non-homogeneous body, in a radiation path, with at least one pulse of radiation of a temporal pulse width $t_p$;

b. selecting said laser temporal pulse width $t_p$ in relation to a combined factor $t_p^* = \kappa \cdot c \cdot t_p$ for a minimum value for said combined factor $t_p^*$ or for a value of said combined factor $t_p^*$ no greater than about 1, where $\kappa$ represents said extinction coefficient of said scattering mediums, and c represents the propagation speed of light radiation through said scattering mediums;

c. receiving said reflected radiation from respective incident points located in said radiation path;

d. producing an indicator for at least one material in said radiation path, responsive to said radiation reflected by said respective incident points.

15. The method of claim 13, wherein, said step of producing said indicator includes, e. producing an indicator of the location of at least one of said respective incident points.

16. The method of claim 13, wherein said step of producing said indicator includes, f. producing an indicator of the optical distance of said respective incident points.

17. The method of claim 16, wherein said step of producing an indicator of the optical distance includes, g. producing data indicative of the amplitude of said radiation reflected from said respective incident points and data indicative of the optical distance t* to said respective incident point, where the optical distance to said respective incident point is $t^* = \kappa \cdot c \cdot t$, and where I represents the distance of said radiation path to said respective incident point and where the effective time t of propagation for said respective incident point is $t = 2I/c$.

18. The method of claim 13, wherein, h. said step of producing one or more pulses of radiation includes the step of producing a single pulse of radiation; and i. said step of producing an indicator includes the step of producing said indicator in response to said single pulse of radiation.

19. The method of claim 13, wherein, said step of producing an indicator comprises, j. producing an indicator indicative of the amplitude of said reflected radiation from said respective incident points and of the optical distance t* to said respective incident points.

20. The method of claim 13, wherein, k. said step of producing an indicator includes the step of producing an indicator for an enclosed material in said path of radiation, enclosed by an enclosing material, in said path of radiation.

21. The method of claim 20, wherein, said step of producing an indicator includes the step of producing a indicator of the size, location or image of said enclosed material enclosed by said enclosing material.

22. The method of claim 20, wherein, said step of producing an indicator includes the step of producing data displaying separate amplitudes for respective incident points in said radiation path and the corresponding optical distances t* of said respective incident points.

23. The method of claim 13, wherein, said step of producing an indicator, comprises,
  l. producing data of the reflected radiation amplitudes of the respective incident points correlated with the optical distance t* to the respective incident points;
  m. displaying said indicator as a change in said data at an interface between an enclosed material enclosed by an enclosing material, of said plurality of materials.

24. The method of claim 23 wherein, said step of producing said indicator includes the step of producing a single pulse of radiation, and said step of producing data includes the step of receiving said reflected radiation substantially about the axis of said path of radiation.

25. The method of claim 13, wherein,
  n. said step of producing said radiation includes the step of producing a single pulse of radiation; and
  o. said step of producing an indicator includes the step of producing an indicator in response to said single pulse of radiation for at least one of said plurality of materials in said radiation path.

26. The method of claim 13, wherein,
  p. said step of producing radiation includes the step of producing radiation in a plurality of radiation paths and said step of receiving said reflected radiation includes the step of receiving reflected radiation from said plurality of radiation paths;
  q. said step of producing an indicator includes the step of receiving reflected radiation from said plurality of radiation paths, and responsive to said reflected radiation, producing said indicator from said reflected radiation from said plurality of radiation paths.

27. An Optical Imaging Apparatus Using A Temporal Direct Reflectance Signal, for detecting in a non-homogeneous body, one or more interfaces between a first material and a second material, with different scattering characteristics relative to each other, comprising,
  a laser operative to produce light in one or more pulses of light radiation, in a light path directed on a non-homogeneous body comprising an enclosing material and an enclosed, in said light path;
  a detector operative to receive reflected light from incident points, on said light path, in said enclosed material and said enclosing material;
  a data acquisition system connected to said laser and said detector for producing data, related to said one or more pulses of light radiation, of the amplitude of said reflected light from respective incident points and of the optical distance to said respective incident points, in said enclosing and enclosed materials;
  said data acquisition system responsive to said data of said amplitude and said data of said optical distance, for respective incident points, and producing data indicative of one or more of said respective incident points on an interface between said enclosing material and said enclosed material;
  said laser operative to produce said one or more pulses of light radiation with a pulse width $t_p$ related to a minimum value, or a value no greater than about 1 for a combined factor $t_p^*$, by $t_p^* = \kappa \cdot c \cdot t_p$, where $\kappa$ represents said extinction coefficient of said first and second materials and c represents the propagation speed of light radiation through said first and second materials; and $t_p$ represents said pulse width; and where the optical distance to said respective incident point is $t^* = \kappa \cdot c \cdot t$, and where I represents the distance of said radiation path to said respective incident point and where the effective time t of propagation for said respective incident point is $t = 2I/c$.

28. The apparatus of claim 27, wherein, said laser is operative to produce said light radiation in a single pulse of light radiation; and said data acquisition system connected to said laser and said detector is operative to produce said data, related to said one or more pulses of light radiation, of the amplitude of said reflected light from respective incident points and of the optical distance to said respective incident points, in said enclosing material and said enclosed material, responsive to said one single pulse of light radiation.

29. The apparatus of claim 27, wherein data acquisition system is operative to direct said light path in a plurality of light paths on a plurality of respective separate locations on said non-homogeneous body;
  said data of said amplitude and said data of said optical distance, for respective incident points, is related to said plurality of light paths;
  said data acquisition system is operative to correlate said data, related to said plurality of light paths, to produce data of a two dimensional or three dimensional image of said enclosed or said enclosing materials.

30. The apparatus of claim 27, wherein, said laser includes a plurality of separate lasers and said detector includes a plurality of separate detectors;
  said data acquisition system is connected to said plurality of separate lasers and is connected to said plurality of separate detectors, to direct said separate lasers in respective light paths on separate locations on said non-homogeneous body, and to said separate detectors to receive said reflected light from said separate locations on said non-homogeneous body, and to correlate said reflected light received by said separate detectors from said respective separate locations;
  said data acquisition system responsive to said reflected light producing data indicative of the amplitude of said reflected light from respective incident points in said respective light paths and to the optical distance to said respective incident points, in said enclosing material and said enclosed material.

* * * * *